US011707352B2

(12) United States Patent
Bou Aoun et al.

(10) Patent No.: US 11,707,352 B2
(45) Date of Patent: Jul. 25, 2023

(54) LOCKING KIT FOR IMPLANTABLE ARTIFICIAL ORGAN (71) Applicant: Defymed, Strasbourg (FR)

(72) Inventors: Richard Bou Aoun, Strasbourg (FR); Charles-Thibault Burcez, Strasbourg (FR); Jordan Magisson, Strasbourg (FR); Séverine Sigrist, Strasbourg (FR); Nicolas Faivre, Besançon (FR); Clément Leonard, Besançon (FR); Sébastien Perrot, Besanç on (FR)

(73) Assignee: DEFYMED, Strasbourg (FR)

( * ) Notice: Subject to any disclaimer, the term of this patent is extended or adjusted under 35 U.S.C. 154(b) by 509 days.

(21) Appl. No.: 16/630,122

(22) PCT Filed: Jul. 10, 2018

(86) PCT No.: PCT/EP2018/068715
§ 371 (c)(1),
(2) Date: Jan. 10, 2020

(87) PCT Pub. No.: WO2019/011943
PCT Pub. Date: Jan. 17, 2019

(65) Prior Publication Data
US 2020/0155294 A1 May 21, 2020

(30) Foreign Application Priority Data

Jul. 12, 2017 (EP) ...................................... 17305923

(51) Int. Cl.
*A61F 2/02* (2006.01)
(52) U.S. Cl.
CPC ...... *A61F 2/022* (2013.01); *A61F 2220/0033* (2013.01)

(58) Field of Classification Search
CPC .............. A61F 2/022; A61F 2220/0025; A61F 2220/0033
See application file for complete search history.

(56) References Cited

U.S. PATENT DOCUMENTS 3,313,289 A * 4/1967 Kapral ................... A61B 10/00
623/66.1
5,314,471 A * 5/1994 Brauker ............... A61K 9/0024
623/23.72
(Continued)

FOREIGN PATENT DOCUMENTS

CA 2279996 A1 * 1/1998 .......... A61M 2/3472
WO WO 00/44424 8/2000
(Continued)

*Primary Examiner* — Paul B Prebilic
(74) *Attorney, Agent, or Firm* — Panitch Schwarze Belisario & Nadel LLP; Erin M. Dunston (57) ABSTRACT The invention relates to a chamber (100) for encapsulating secreting cells producing at least one substance of interest, the chamber comprising: —an upper washer (120) and a bottom washer (110) configured to be oppositely placed on a side and on another side of two semi-permeable membranes (141, 142), —optionally at least one intermediate washer (130), provided between both membranes, in a plane sensibly parallel to upper and bottom washers planes and delimiting two superposed half cells spaces (S1, S2) capable of containing the secreting cells producing the at least one substance of interest, —optionally sealing means (150) the upper and the bottom washers (120, 110) being tightly clipped together, incorporating the intermediate washer (130) therebetween.

15 Claims, 3 Drawing Sheets (56) References Cited

U.S. PATENT DOCUMENTS 5,957,895 A     9/1999   Sage et al.
8,834,979 B2 *  9/2014   Piranda .................... A61F 2/02
                                                  424/424

FOREIGN PATENT DOCUMENTS

WO     WO 2008/083209     7/2008
WO     WO 2008/103101     8/2008

* cited by examiner

LOCKING KIT FOR IMPLANTABLE ARTIFICIAL ORGAN

CROSS-REFERENCE TO RELATED APPLICATIONS

This application is a U.S. National Stage Application pursuant to 35 U.S.C. § 371 of International Patent Application PCT/EP2018/068715, filed on Jul. 10, 2018, and published as WO 2019/011943 on Jan. 17, 2019, which claims priority to European Patent Application 17305923.9, filed on Jul. 12, 2017, all of which are incorporated herein by reference in their entireties for all purposes.

FIELD OF THE INVENTION

The invention relates to the field of implantable pouches made with semi-permeable membranes, for distributing molecules of interest in situ, and in particular to a chamber for encapsulating secreting cells of bioartificial organs which are implantable and in particular which are in the form of chambers for encapsulating cells secreting a substance of interest.

BACKGROUND

The treatment of pathological conditions requiring a continuous supply, to the body, of substances of interest has made necessary the development of devices which can be implanted in a patient and are capable of releasing these substances efficiently and sometimes for long periods of time.

To satisfy this need, one can use bioartificial organs which contain cells producing one or more substances of interest. The cells contained in a bioartificial organ are confined in internal spaces, or implantable chambers, delimited by at least one semi-permeable membrane. Such a membrane is termed "semi-permeable" when it allows the diffusion of the substances of interest out of the chamber to the target cells in the patient's body, while at the same time being impermeable to the antibodies and the cells of the patient's immune system, thus preventing them from directly attaching the cells producing the substance(s) of interest.

Alternatively, one can deliver the substance of interest through a chamber delimited by at least one semi-permeable membrane, with a catheter arriving to the chamber and delivering the compound of interest within the chamber, the compound of interest being able to diffuse through the semi-permeable membrane to the patient's body. In this embodiment, the membranes may not necessarily be impervious to the molecules of the immune system (such as antibodies or cytokines). In this embodiment, the substance of interest is any compound that is injected to a patient for treating the patient. It can be, in particular, a growth hormone (for treating dwarfism), a coagulation factor (for treating hemophilia), a cytokine or the like (tumor-necrosis factors, interferons . . . ) or an anti-inflammatory molecule (whether nonsteroidal or steroidal) useful for treating auto-immune diseases such as arthritis, ankylosing spondylitis, multiple sclerosis, celiac disease, Graves disease, inflammatory bowel disease, psoriasis, rheumatoid arthritis, and systemic lupus erythematosus, heparin or heparinoids useful for treating coagulation, a compound used in immuno-therapy, a drug used in chemotherapy, an immunosuppressing drug (such as for treating Graft vs Host rejections), an antiviral drug, arsenic (some auto-immune diseases), TNF (useful for hepatitis C), dopamine (for Parkinson disease treatment), eptifibatide (for reducing the risk of acute cardiac ischemic events and treating heart failure), a beta blocker drug.

A bioartificial organ is understood to be a device, in particular intended to be implanted in a patient, comprising at least one encapsulating chamber consisting of at least one semi-permeable membrane; said encapsulating chamber is intended to contain cells which secrete one or more substance(s) of interest.

A substance of interest is any substance intended to have a beneficial effect in the patient. This may therefore be a neurotransmitter, a hormone, a growth factor, a coagulation factor or a cytokine. In particular, such a substance may be, without any limiting nature, insulin, glucagon, growth hormone, coagulation factor IX, coagulation cofactor VIII or calcitonin.

Examples of devices (bioartificial organs, encapsulating chambers) are known in the prior art. One of these devices is, for example, described in WO2012/010767. This document describes a pouch, or chamber, for forming an implantable artificial organ. This pouch comprises a closed envelope made of a semi-permeable membrane and a sheet contained in the envelope and comprising protuberances so as to maintain a space for cells between the sheet and the envelope.

This pouch has relatively large surface. Indeed, this pouch, as the bioartificial organs in general, must be able to contain a large number of cells, in order to be able to have a prolonged physiological effect after implantation in the patient. However, such relatively large surface of the pouch has the drawback that it risks folding and/or tearing after implantation due to the patient's movements. This may also lead to sedimentation of the encapsulated cells, which is deleterious for the functionality and survival of the cells.

Further, because of the locking mechanism, the pouch, or chamber, of WO2012/010767 presents a risk of ballooning, i.e. a distortion of the pouch from an original flat form to a balloon-like shape due to the penetration of fluid within the pouch.

WO2000044424 discloses subcutaneous implantable ports. The chambers disclosed in D1 don't have semi-permeable membranes.

WO2008083209 discloses a hypodermic drug delivery apparatus comprising a reservoir and a rupturing member. This document is not concerned with implantable chambers made with semi-permeable membranes for diffusing in situ some compound of interest.

WO2008103101 discloses a implant assembly comprising a frame structure with various frames, such assembly comprising a semipermeable membrane or barrier. This document doesn't disclose the assembly proposed herein.

U.S. Pat. No. 5,957,895 discloses a device for delivering a liquid therapeutic preparation into the body of a patient by injection into or through the skin of the patient, with a housing having a bottom surface to be brought into contact with the skin of the patient, a reservoir disposed within the housing and an injection needle disposed generally horizontally in the housing, and adapted to communicate with the reservoir. This document is not concerned with implantable chambers.

Incidentally, there is a need to make available to surgeons novel bioartificial organs or chambers which exhibit, in particular, the possibility to either flush the inside of the pouch in order to replace the cells (e.g. dead cells) without any chirurgical act, or deliver the compound of interest in situ through a catheter that would link the pouch to an external delivery device (pump, syringe, pen, or the like).

SUMMARY OF THE INVENTION

In response to the above formulated problems of the ballooning risks, the applicant is proposing an implantable chamber, or implantable pouch, for providing and diffusing a substance of interest in situ, wherein an inner space is defined by two membranes that are superposed in between two tightly clipped washers. These membranes are sealed at their periphery (preferably heat-welded together), defining an inner space, and the non-inflated chamber is thus essentially flat. Use of these washers is particularly advantageous to avoid the phenomenon of ballooning (which is a consequence of the fact that the membranes are flexible), and upon design of the washers according to specific embodiments, to make it possible to flush and replace the content of the chamber. In particular, the substance of interest is produced in situ by cells encapsulated in the chamber.

According to a first aspect, the invention concerns a chamber delimited by a semi-permeable membrane, for delivering molecules of interest, in particular for encapsulating secreting cells producing at least one substance of interest, or delivering a substance of interest by diffusion through the membranes at the site of implantation, from an external source. The chamber comprises an upper washer and a bottom washer configured to be oppositely placed on a side and on another side of the semi-permeable membranes on each side of the chamber. In a preferred embodiment, the chamber also comprises at least one intermediate washer, provided between both membranes, in a plane sensibly parallel to upper and bottom washers planes. The upper and the bottom washers are tightly clipped together, incorporating the intermediate washer therebetween, in case it is present.

In a specific embodiment, the intermediate washer comprises protrusions, or rises and dips (such as crenels). When only one intermediate washer is present, it is preferred when said intermediate washer has at least one side with protrusions, preferably both sides. When two intermediate washers are present, the protrusions extend on at least one face of each of the intermediate washer. Preferably, such protrusions extend only on one face of each of the intermediate washer, and these faces harbouring the protrusions are facing each other upon assembly. Such protrusions make it possible to maintain a minimal space between the membranes (heights of the protrusions) and minimize the risk of the upper and bottom membranes to stick to each other when the pouch is emptied. In particular embodiments, the upper washer is designed as to allow communication between the inside of the pouch and the outside of it, in particular to transport fluid from an external source within the inner space of the chamber. In this embodiment, the presence of the rises and dips of the intermediate washer makes it possible to allow a repartition of the fluid in all directions and homogenous filling of the pouch.

In the following description, the upper and bottom membranes are semi-permeable membranes. A semi-permeable membrane used herein, is a membrane, made from any biocompatible material that separates a biological solution from another biological environment and allows certain molecules to pass through it. The semi-permeable membrane has a cut-off threshold, the molecules having a weight above this cut-off threshold being unable to cross the membrane, while the molecules having a weight below this cut-off threshold can cross the membrane. The determination of the cut-off threshold is carried out by those skilled in the art according to the characteristics of the molecules that they wish to stop or allow to penetrate. Such membranes are disclosed in particular in WO2016184872 and WO2015086550. In particular, the membranes comprise at least one layer of porous biocompatible polymer, and one layer of non-woven biocompatible polymer. Pore densities and sizes are disclosed in particular in WO2016184872 and WO2015086550.

In one preferred embodiment, and in order to allow the passing of small molecules such as insulin, glucagon or glucose and to stop the effector molecules of the immune system (such as antibodies and complement factors), this cut-off threshold is between 40 kDa and 500 kDa, or between 100 kDa and 500 kDa, or between 100 kDa and 150 kDa, more preferably between 50 kDa and 150 kDa.

The internal diameter of the pores of the porous polymer makes it possible to obtain the desired cut-off threshold. Thus, in one particular case, the internal diameter of the pores present on the layer of porous biocompatible polymer is between 5 and 100 nm, entirely preferably between 5 and 50 nm.

Advantageously, the bottom washer comprises at least two blades extending in planes sensibly orthogonal to upper and bottom washers planes, the upper washer comprises housings for receiving free ends of the blades in order to clip the upper washer with the bottom washer, and the intermediate washer (if present) and the membranes comprise first openings arranged to be crossed by the blades. The first opening of the membranes can be designed so as to only allow crossing of the blades (they have the same diameter than the outer distance between the blades). However, it is preferred when the first opening of the membranes consist in a whole hole in the membranes, the diameter of which being adapted so as to allow the passage of the blades, the upper and bottom washer fully covering said holes of the membranes.

Such a configuration allows, among other advantages, to maintain the chamber in place around the semi-permeable membranes and to support the sheet allowing space between it and the membranes.

Advantageously, the chamber comprises sealing components disposed between the upper washer and one membrane and between the bottom washer and the other membrane. These sealing components help to obtain a tight clipping and also avoid damage on the membrane which could be due to the upper and bottom washer pressing on the membrane. These sealing components are in any appropriate biocompatible material, such as silicone.

It is preferred when the intermediate washer presses the sealing component. As shown in the examples, this embodiment makes it possible to increase tightness of the chamber for higher pressures than when such configuration is not present.

Advantageously, the intermediate washer comprises at least one second opening adapted to fluid circulation within the inner space of the chamber.

Advantageously, the second opening is provided in the center of the intermediate washer, the first openings being disposed around the second opening.

According to one or more embodiments, each of the blades comprises, at their free end, a through-hole adapted to be crossed by a pin in order to tightly clip the upper washer with the bottom washer, and tight clipping is thus performed by the pin extending across the holes in the free ends of the blades.

According to one or more embodiments, the upper washer comprises an elevated height provided with a longitudinal cavity opening between both blades of the bottom washer.

Advantageously, the pin is a hollow pin extending in the longitudinal cavity, that it able to transport fluid from an outside source within the inner space of the chamber. The pin comprises a proximal end (intended to be inserted within the hole at the free end of the blades) and a distal end that are connected by a hollow body of which the distal end is open and the proximal end is closed, said first hollow body having at least one orifice arranged near the distal end. In this matter, an extremity of a catheter can be positioned at the distal end of the pin, whereas the other extremity of the catheter is connected to an external delivery device (pump, syringe or the like). This makes it possible to either empty and fill the chamber (for instance to replace cells which are encapsulated herein) or to continuously or from time to time directly deliver a substance of interest for in situ diffusion through the membranes of the chamber. The fluid passing through the hollow body and the orifice enters the housing and the chamber through a hole (orifice) in the upper membrane that links the housing of the upper washer to the inside of the chamber. In case an crenelated intermediate washer is present, such crenels improves the diffusion of the fluid in all (x,y) directions within the chamber.

According to one or more embodiments, the upper washer, the bottom washer and the intermediate washer are sensibly disk-shaped.

According to one or more embodiments, the chamber comprises two intermediate washers provided in parallel planes, each of the intermediate washers preferably comprising protrusions, or rises and dips (such as crenels), extending on at least one face facing the other intermediate washer. Preferably the intermediate washers comprise such rises and dips on both faces. As indicated above, the configuration is that the intermediate washer shall press the sealing component or the upper and bottom washer upon clipping of the system, and improve tightness and pressure resistance between the inside and outside of the pouch.

According to one or more embodiments, and especially when the chamber is intended to receive secreting cells, the chamber comprises a foil disposed between both membranes as disclosed in WO2012/010767 (U.S. Pat. No. 8,834,979). The foil will preferably comprise protuberances on one or preferably on both of its faces. As in U.S. Pat. No. 8,834,979, the protuberances may have the shape of dashes spaced apart from one another and forming regularly distributed lines parallel to one another. This arrangement defines channels in the direction in which the fluids may easily circulate, channels being oriented, for some, in the direction of the dashes, and, for others, obliquely with respect to said dashes. In another embodiment, the protuberances are in staggered rows, thus creating channels that form parallel lines perpendicular to other parallel lines.

In this embodiment, the foil (or sheet) defines two half spaces within the inner space of the chamber. This embodiment is particularly preferred when the chamber is intended to contain cells producing one or more substances of interest. Such cells would thus be present in the two half-spaces and would more easily settle along the sheet, rather than form cell aggregates, and improving diffusion of oxygen and nutrients to the cells inside the chamber, thus limiting the stress of the cells and improving survival thereof.

In this embodiment, the foils contain first openings to be crossed by the blades and preferably a second opening to allow fluid circulation within the inner space of the chamber, between the two halve-spaces.

According to a second aspect, the invention concerns a kit connector comprising:

an upper washer and a bottom washer that can tightly be clipped together wherein the bottom washer comprises at least two blades extending in planes sensibly orthogonal to the bottom washers plane, the upper washer comprises housings for receiving free ends of the blades and wherein each of the blades comprise, at their free end, a through-hole adapted to be crossed by a pin in order to tightly clip the upper washer with the bottom washer, and tight clipping is thus performed by the pin extending across the holes in the free ends of the blades, the upper washer and bottom washer being sensibly in parallel planes after clipping;

optionally at least one intermediate washer, incorporated between the upper and the bottom washers, in a plane sensibly parallel to upper and bottom washers planes;

optionally sealing components and a pin, that can extend through the through-holes to tightly clip the two washers In a preferred embodiment, the pin is a hollow pin, as disclosed above and the upper washer presents the elevated height as disclosed above, so that the pin can be used to transport fluid from an outside source within the elevated height (and within the inner chamber when the connectors are assembled with the membranes).

According to a third aspect, the invention concerns a method for making the above defined chamber, comprising the following steps:

providing the bottom washer on one side of a first membrane comprising a first opening;

optionally providing a silicone O-rings between the bottom washer and the membrane.

crossing the blades of the bottom washer into the first opening of the first membrane;

optionally providing at least one intermediate washer above the first membrane with the blades crossing the first openings;

providing a second membrane comprising another first opening above the intermediate washer with the blades crossing said other first opening;

optionally providing a silicone O-ring between the second membrane and the upper washer.

providing the upper washer upon the second membrane with housings slotted on free ends of the blades; and providing a pin, preferably a hollow pin, within a longitudinal cavity of the upper washer, and crossing the through-hole of each of the blades in order to tightly clip the upper washer with the bottom washer.

The invention also relates to a method of circulating a fluid within or from an implantable chamber comprising the step of circulating a fluid through a catheter linked to the distal end of a hollow pin locked in the blades, wherein the pin comprises the above-mentioned aperture, close to its proximal end, opening into the above-mentioned through housing thereby allowing circulation of the fluid within or from the implantable chamber through the first openings.

This method may be performed in vitro or in vivo when the chamber has been implanted. It is particularly adapted to empty the pouch of dead or inactive cells and refill it with new live cells. This makes it possible to replace cells within an implantable chamber. It is also adapted to deliver a substance of interest within the pouch for in situ diffusion through the membranes.

Further Description of the Chamber

The chamber may comprise more than one connector system as disclosed herein. These are preferably placed regularly over the surface of the chamber to obtain a cushion-like effect.

Membranes

The semi-permeable membranes are made from one or more layer of biocompatible polymer(s), with at least one layer that is porous, in order to control the size of the molecules that can cross the membranes.

Material

Such membranes are disclosed in particular in WO2016184872 and WO2015086550.

In particular, the membranes comprise at least one layer of porous biocompatible polymer, and one layer of non-woven biocompatible polymer.

Porous biocompatible polymers are known in the art. It may be chosen from polycarbonate (PC), polyester, poly-ethyleneimine, polypropylene (PP), poly(ethylene terephthalate) (PET), poly(vinyl chloride) (PVC), polyamide and polyethylene (PE), polyether sulfone (PES).

In one particular embodiment, at least one layer or more layers, as appropriate, is (are) made of poly(ethylene terephthalate) (PET).

As indicated, and for greater mechanical stability, the porous biocompatible polymer membrane may be reinforced by a membrane made of non-woven. The combination of a non-woven polymer and of the porous membrane of biocompatible polymer is preferentially carried out by lamination, using methods known in the art, such as thermal lamination, with or without the presence of adhesives, preferably without adhesive.

In a specific embodiment, the membrane consists of two layers of porous biocompatible polymer surrounding a layer of non-woven.

It is recalled that a non-woven polymer (non-woven) is such that the fibers thereof are maintained randomly. It is thus a sheet consisting of fibers oriented in a particular direction or randomly, bonded by friction and/or cohesion and/or adhesion. The fibers are thus arranged statistically, i.e. deposited randomly. Consequently and due to the random arrangement of the fibers, the non-woven polymer is permeable to substances, and there is no control of the size of the substances that can diffuse within the non-woven polymer. Non-woven polymers can be produced using polymeric fibers of any type. Mention may thus be made of polyesters: PET (poly(ethylene terephthalate)), PBT (poly(butylene terephthalate)), PVC (poly(vinyl chloride)), PP (polypropylene), PE (polyethylene) or blends of these polymers.

It is also to be noted that, without the treatment to make a biocompatible polymer porous, such polymer would remain impervious to any substance, and would not allow diffusion of the substance of interest from the inner part of the biocompatible organ to the outer part. The pores only allow the diffusion of substances that are below the cutoff (i.e. that are smaller than the pore diameter).

Pore Density and Size

Pore densities and sizes are disclosed in particular in WO2016184872 and WO2015086550.

Pore density is generally greater than $10^6$ pores/cm$^2$, preferably greater than $10^7$ pores/cm$^2$. This pore density is generally less than $10^{11}$ pores/cm$^2$, preferably less than $10^{10}$ pores/cm$^2$. Use is therefore made of membranes which can have a pore density preferentially greater than $10^6$ pores/cm$^2$, more preferably greater than $10^7$ pores/cm$^2$. This density is preferentially less than $10^{11}$ pores/cm$^2$, or even less than $10^{10}$ pores/cm$^2$. This density is therefore between $10^6$ pores/cm$^2$ and $10^{11}$ pores/cm$^2$. A density greater than $10^9$ and less than $10^{10}$ pores/cm$^2$ is perfectly suitable.

At least one of the two layers (or the only layer if such is the case) of porous biocompatible polymer has pores which have an internal diameter greater than 5 nm and preferably greater than 10 nm, and less than 100 nm, and preferably greater than 10 nm and less than 50 nm, more preferably less than 40 nm. It has also been observed that a pore diameter of less than 90 nm at the surface of the membrane is also very favorable for this layer of porous biocompatible polymer, as such pore diameter maintains the semi-permeability property, that is sought for the membrane. The pore density is then advantageously greater than $2.10^9$ and less than $4.10^{10}$ pores/cm$^2$.

When the membrane has two layers of porous biocompatible polymers, the internal diameter of the pores of one of the layers is preferentially as above.

The internal diameter of the pores of the second layer may be larger, the cut-off effect at the desired size being given by the diameter of the pores of the first layer. Thus, the internal diameter of the pores of the second layer may be greater than 100 and less than 2000 nm, preferably greater than 200 nm. These pores preferably have an internal diameter less than 1000 nm. An internal pore diameter greater than 400 and less than 600 nm, or of approximately 500 nm, is perfectly suitable. The pore density is then advantageously greater than $5.10^6$ and less than $5.10^7$ pores/cm$^2$.

When the membrane comprises two layers of porous biocompatible polymer, which surround the layer of non-woven, it is preferable for the encapsulating chamber to be such that the layer for which the pore diameter is the smallest is situated inside the chamber (in contact with the secreting cells producing at least one substance of interest) and that the layer for which the pore diameter is the widest is situated on the outside (in contact with the patient's body).

Thickness of the Membranes

When the membrane comprises only one layer of porous biocompatible polymer, the thickness of the membrane is preferably higher than 5 µm and lower than 250 µm, and more preferably comprised between 5 µm and 200 µm, or between 5 µm and 50 µm.

When the membrane is made of various layers of biocompatible polymers, such as non-woven and porous biocompatible polymers, the thickness of the membrane is preferably as disclosed in WO2016184872 and WO2015086550.

In particular, the total thickness of the membrane (comprising the layer of non-woven polymer and the layer(s) of porous polymer(s)) is greater than 45 µm. It is generally, and preferably, less than 250 µm, but can also be greater than this size; thicknesses ranging up to 300 µm, or even beyond, can in particular be envisaged. Preferably, it is greater than 50 µm. It is also preferentially less than 150 µm. This membrane thus generally has a thickness of between 45 and 250 µm.

The layer of non-woven polymer generally has a thickness greater than 40 µm, preferably greater than 60 µm, more preferably greater than 80 µm. This layer has a thickness generally less than 250 µm and preferably less than 150 µm. Thus, the thickness of the layer of non-woven polymer is often between 40 µm and 150 µm.

In this embodiment, and when the membrane has only one layer of biocompatible polymer, said layer then has a thickness greater than 5 µm. This layer is less than 250 µm, preferably less than 100 µm, being, however, preferably less than 50 µm.

When the membrane has two layers of porous biocompatible polymer, these layers may have the same thickness. In another embodiment, said layers have different thicknesses. It is then preferred when the thickness of the inner layer is greater than 5 µm. It is also preferably less than 250

µm, but preferably less than 40 µm; a thickness less than 15 µm (and preferably greater than 5 µm) is perfectly suitable. The thickness of the second (outer) layer is generally greater than 25 µm. It is preferably less than 250 µm, preferably less than 100 µm, more preferably less than 50 µm; a thickness of between 30 and 50 µm is perfectly suitable.

Shape of the Chamber

In one preferred embodiment, the encapsulating chamber is circular, as this shape lacks "corners" or protruding parts, capable of creating cell or inflammatory aggregates during the implantation, and is easy when manufacturing the encapsulating chamber (no need to orient the two membranes).

In one particular embodiment, the diameter of the encapsulating chamber is greater than 5 cm, preferably greater than 8 cm. It is generally less than 20 cm, and is preferentially less than 15 cm, or than 14 cm. A diameter of between 5 and 14 cm is perfectly acceptable.

When the chamber is not round, the largest dimension thereof is generally greater than 3 cm, preferably greater than 5 cm, or than 8 cm. It is generally less than 20 cm, and is preferentially less than 15 cm, or than 14 cm.

Volume of the Chamber and Cells

As seen above, the encapsulating chamber preferentially is intended to contain secreting cells producing at least one substance of interest, and to allow said cells to secrete this substance for a considerable period of time (greater than 3 months, preferentially greater than 6 months) at levels which are of physiological interest (i.e. making it possible to meet the patient's need).

The preferred internal volume of the encapsulating chamber should be greater than 15 ml, preferably greater than 20 ml, more preferably greater than 25 ml, and can rise to 50 ml, for use in humans.

Such encapsulating chambers must be able to contain a large number of cells. In the context of the treatment of diabetes, it must be possible to encapsulate the equivalent of at least 500 000 islets of Langerhans, preferably the equivalent of more than 700 000 islets, and optionally up to the equivalent of one million islets of Langerhans. In the knowledge that one islet contains, on average, about 1000 cells, this gives an estimation of the number of cells that the encapsulating chamber according to the invention can contain.

The number of cells will obviously vary according to the type of cells that it is desired to encapsulate and implant in the patient.

PREFERRED EMBODIMENT

In one preferred embodiment, the membrane forming the encapsulating chamber comprises two layers of porous biocompatible polymers on either side of the non-woven polymer. In this embodiment, it is preferred for at least the internal layer (situated inside the chamber after formation of the chamber) to be the layer on which the pores provide the semi-permeable nature of the membrane (cut-off threshold), i.e. which has the pores that have an internal diameter greater than 5 nm (and generally less than 100 nm) or having the other dimensions mentioned above.

The layer external to the shell (in contact with the patient's tissues and cells) can have pores with a larger internal diameter, in particular greater than 100 nm, but preferably less than 2000 nm, or having the other dimensions mentioned above.

Dimension of the Connectors

With reference to the figures, the bottom washer 110 has generally a diameter between 9.5 and 10.8 cm, more preferably between 9.8 and 10.5 cm.

The blades 111, 112 have generally a height comprised between 3.8 and 5 cm, preferably between 4.6 and 5 cm.

The diameter of the cavity 122 on the washer 120 is generally comprised between 1.2 and 1.5 cm.

BRIEF DESCRIPTION OF THE DRAWINGS

A detailed description of some preferred embodiments is set forth herein below with reference to the following drawings, in which.

DETAILED DESCRIPTION

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example" means that a particular feature, structure, or characteristic described is included in at least one embodiment described herein and does not imply that the feature, structure, or characteristic is present in all embodiments described herein.

Figure 1:
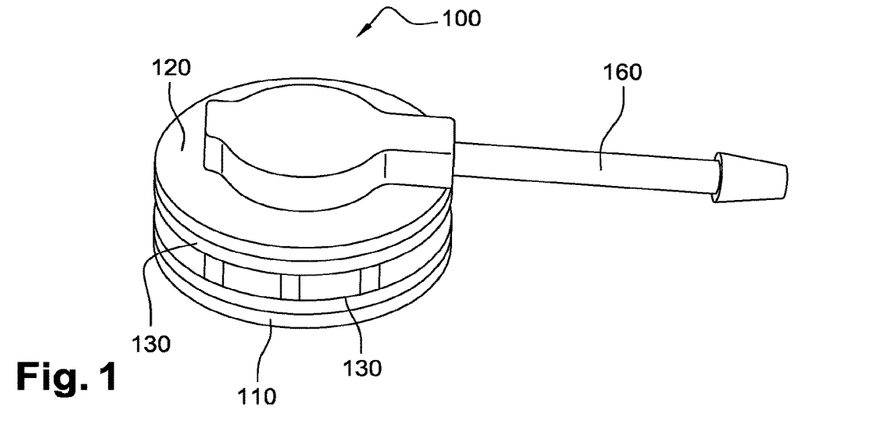
FIG. 1 is a perspective view of an assembled kit connector according to one or more embodiments.

FIG. 1 is a representation of a kit connector intended to be associated to semi-permeable membranes for forming an implantable chamber which can be used for encapsulating secreting cells producing at least one substance of interest. In this figure, the connector is assembled. This connector, referenced 100, comprises an upper washer 120 and a bottom washer 110 made for example in a thermoplastic material such as PEEK (PolyEtherEtherKetone). The upper washer 120 is configured to be placed on a side of a first semi-permeable membrane (non-visible on FIG. 1). The bottom washer 110 is configured to be placed on a side of a second semi-permeable membrane (non-visible on FIG. 1). Thus, the upper washer 120 and the bottom washer 110 are oppositely placed on both sides of both semi-permeable membranes and are arranged to be tightly clipped together.

Further, FIG. 1 shows two intermediate washers 130, for example in PEEK, provided between both semi-permeable membranes, in a plane sensibly parallel to upper and bottom washer planes. In some embodiments, represented on FIG. 3B, only one intermediate washer 130 is provided. In other embodiments, as represented on FIG. 2A and FIG. 3A, two intermediate washers 130 are provided between the first and the second semi-permeable membranes. When a silicone sheet 170 is provided, as shown in FIG. 3A, the connector kit maintains it within the inner space of the chamber.

Figure 2A:
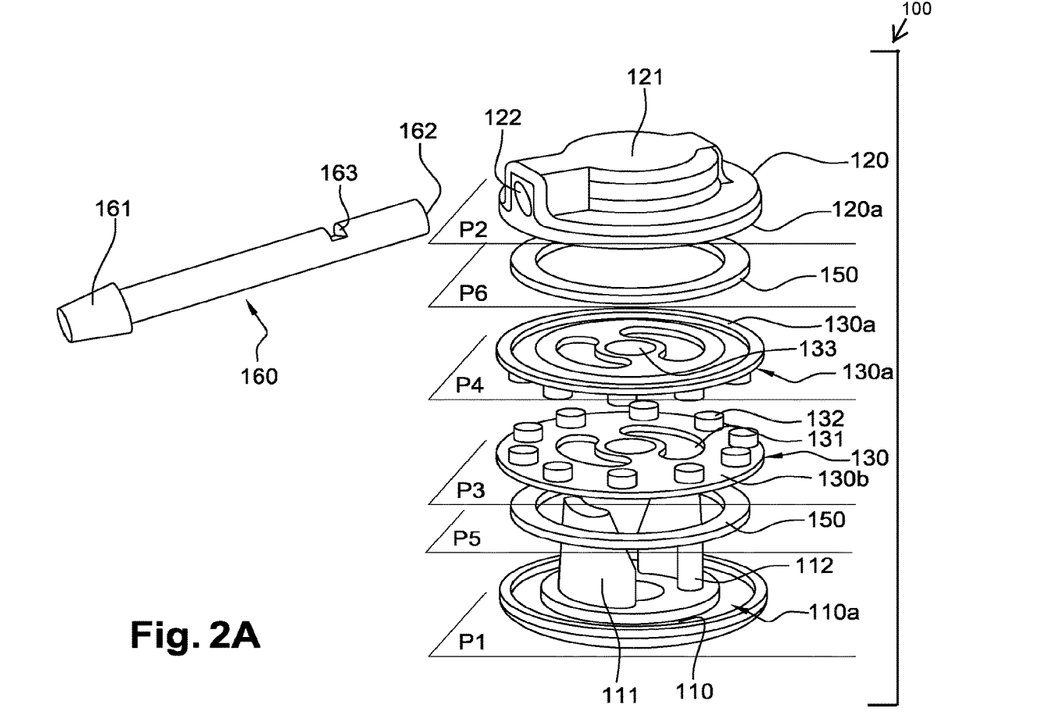
FIGS. 2A-2B are exploded views of the kit connector of FIG. 1.
Figure 2B:
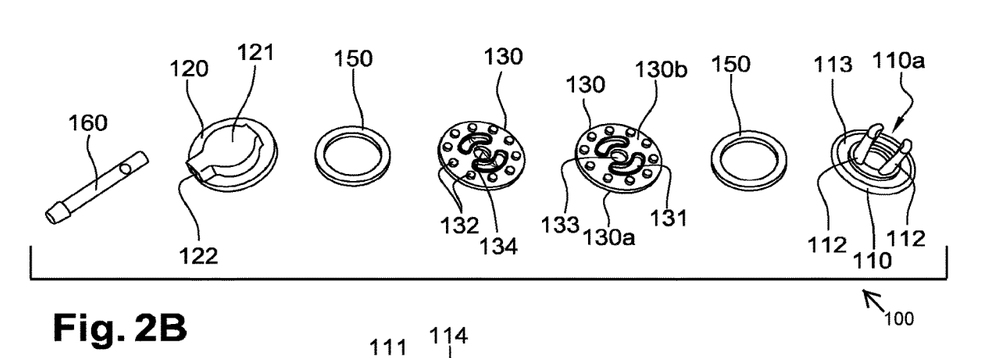
Figure 3A:
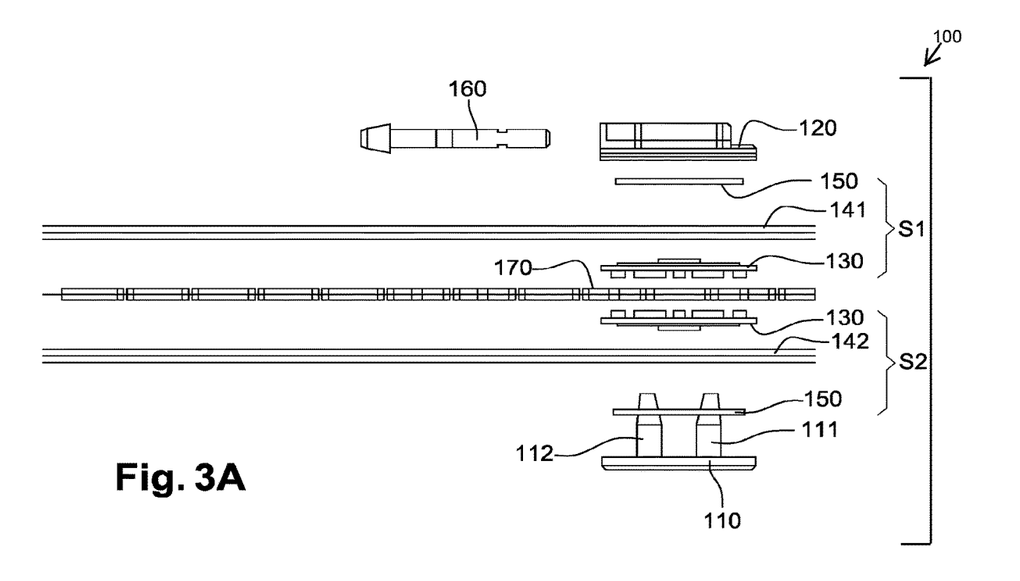
FIG. 3A-3B are side views of two embodiments of an implantable chamber comprising the kit connector of FIG. 1.
Figure 3B:
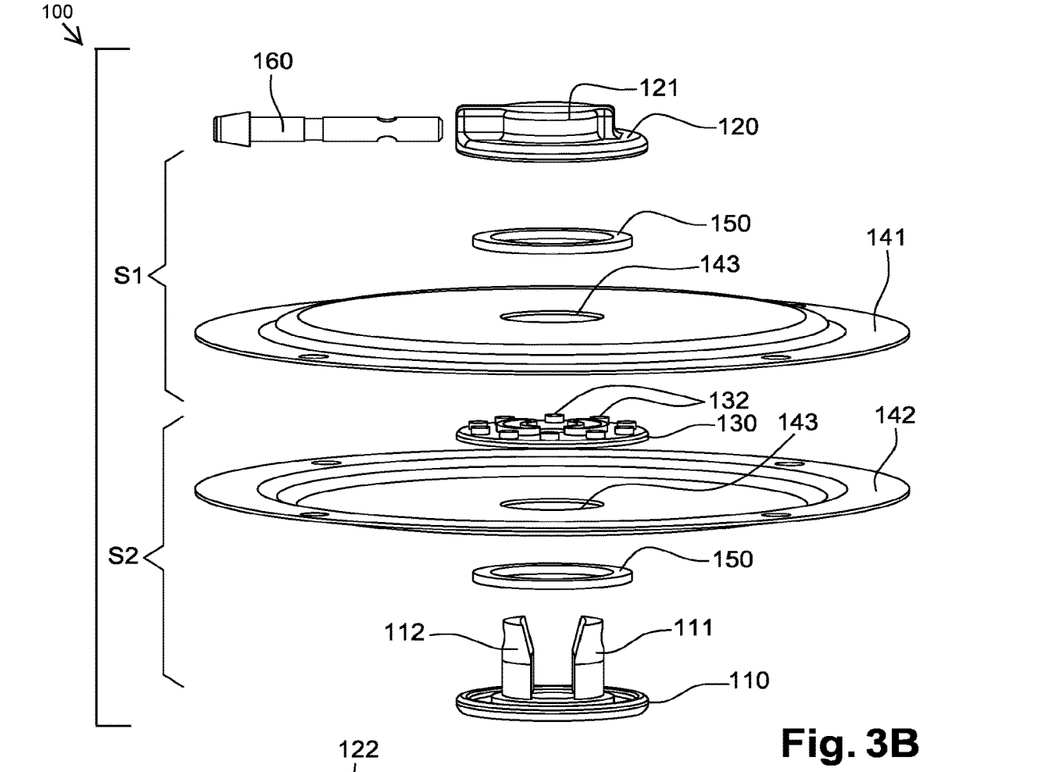

The intermediate washer 130 may be of the same external dimension as the upper and the bottom washers, like represented on FIGS. 2-3. Alternatively, the intermediate washer 130 may be of smaller or larger dimension than the upper and the bottom washers.

FIGS. 2A and 2B show how the different components forming the connector kit are assembled with the membranes that would be between the sealing components 150 and the intermediate washers 130. FIG. 3A shows, in particular, the relative position of these components in respect to the semi-permeable membranes 141, 142, called also simply membranes. Mainly, the upper washer 120 is intended to cover a part of the first membrane 141, the bottom washer 110 is intended to be below a part of the second membrane 142 and the intermediate washers 130 are intended to be positioned between the first and the second membranes 141, 142. Thus, the upper washer 120 and the bottom washer 110 are face to face on the outside of the membranes 141, 142 and the intermediate washers 130 are placed inside of the space delimited by the membranes. Sealing components such as O-rings (150) are placed between the upper and bottom washers and their respective membranes. It thus appears that the washers don't cover the whole surface of the semi-permeable membranes.

The bottom washer 110 comprises two or more blades extending in planes sensibly orthogonal to the upper and bottom washers planes P1, P2. Therefore, as all the washers 110, 120, 130 and the membranes 141, 142 are in parallel planes, respectively P1, P2, P3-P4, P5-P6, the blades 111, 112 are relatively perpendicular to all these planes P1-P6. The blades 111, 112 may take, for example, the shape of fins or the shape of a portion of cylinder or portion of cone or every shape allowing a stable connection between the upper washer and the bottom washer. These blades 111, 112 are configured to cross over the intermediate washers 130 and the membranes 141, 142 and to be lodges into the upper washer 120.

In the disclosed embodiment, the upper washer 120 comprises an elevated height 121 which may extend on the complete surface of the upper washer 120 or on a portion of the upper washer surface, as shown on FIGS. 2A-2B.

Figure 5A:
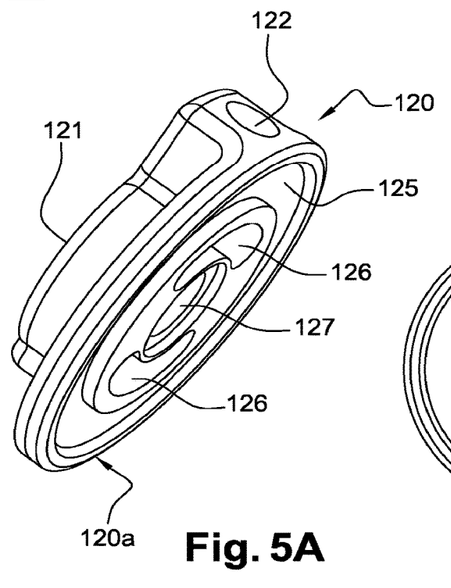
FIG. 5A-5B are a perspective view and a bottom view, respectively, of the upper washer of the kit connector of FIG. 1.
Figure 5B:
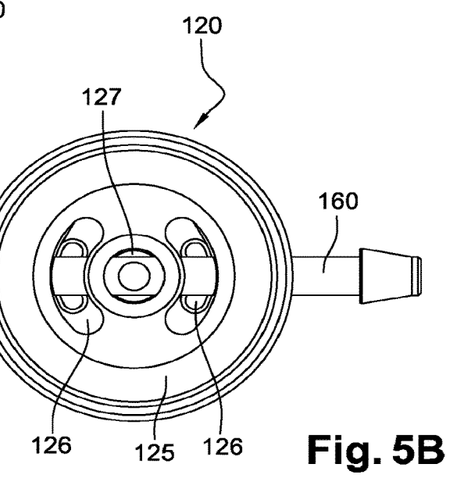

As represented on FIGS. 5A-5B, the elevated height 121 of the upper washer 120 includes several housings 125, 126, 127 on its internal face 120a. The housings 126, having a half moon-like shape, are adapted to receive the free ends of the blades 111, 112 in order to connect and clip the upper washer 120 with the bottom washer 110. The housings 125, 127 will be described later.

Further, each intermediate washer 130 comprises first openings 131 configured to be crossed by the blades 111, 112. These openings 131 have a half-moon-like shape adapted to the external shape of the blades 111, 112.

Further, each membrane 141, 142 comprises openings 143 configured to be crossed by the blades 111, 112. These openings 143, placed in regards to the blades 111, 112, are of forms and dimensions adapted to be crossed by said blades. Thus, the blades 111, 112 extend from the bottom washer 110 to the upper washer 120, crossing over the intermediate washers 130 and the membranes 141, 142. Diameter of these openings is approximately equal to the diameter of a circle that would be formed by the half-moon openings 131, namely the distance represented by the arrow 134 in FIG. 2A.

In particular, the openings (143) of the membranes are aligned with the first and second openings of the intermediate washer for allowing the fluid circulation within the chamber.

In some embodiments, the upper washer 120 comprises a peripheral housing 125 in its internal face 120a that serves as a lodge for the silicone O-ring insuring the tightness and protection of the membranes.

Indeed, according to one or more embodiments, the connector 100 comprises sealing components 150 disposed, respectively, between the upper washer 120 and the first membrane 141 and between the bottom washer 110 and the second membrane 142. The sealing components 150 may be, for example, silicone rings housed in adapted grooves. The grooves may be provided in the internal face 110a of the bottom washer 110 (see e.g. groove 113 on FIG. 2B) and/or in the internal face 120a of the upper washer 120 (groove 125 on FIG. 5) and/or in the faces 130a of the intermediate washers 130 which are in contact with the membranes 141, 142. These sealing components 150 allow the upper and the bottom washers to be tightly connected together and help avoiding damage on the semi-permeable membranes during manufacturing processes.

According to the embodiments where two intermediate washers are present, each intermediate washer 130 comprises a first face 130a provided to be in contact with one of the membrane 141, 142. This first face 130a, turned to the upper washer 120, may comprise a groove ensuring tightness. Each intermediate washer 130 comprises further a second face 130b, provided to be turned to the other intermediate washer 130. This second face 130b may comprise protrusions, or rises and dips (such as crenels), 132 generating a free space between both intermediate washers 130 for further improving fluid spread inside the chamber.

In the embodiments presenting only one intermediate washer, said intermediate washer 130 comprises protrusions, or rises and dips, 132 on at least one face and preferably on both faces for generating free spaces with each membrane.

According to one or more embodiments, the elevated height 121 of the upper washer 120 includes a longitudinal cavity 122 opening into the area between both blades 111, 112. For that, the upper washer 120 comprises a through housing 127 connected with the longitudinal cavity 122. The longitudinal cavity 122 may be a hollow area or a duct formed in the elevated height 121 of the upper washer 120, adapted to conduct fluid into the inner volume of the chamber.

Indeed, when the chamber is intended to contain cells secreting the substance of interest, there may be a need to regularly flush the inside volume from the cells—for example, the dead cells—and reinject new cells. In this embodiment, it is preferred when the chamber presents two connectors as herein disclosed to improve flushing and filling of the chamber.

When the chamber is used to deliver a substance of interest in situ at the implantation site, there is a need for delivering a stream of such substance of interest within the chamber. In this embodiment, the chamber may contain only a single connector.

The longitudinal cavity 122 may be used for providing or removing fluid—e.g. medium containing cells or a substance of interest—into/from the half molecules spaces S1, S2. As an alternative, the longitudinal cavity 122 may be used to receive a hollow pin 160 extending into said longitudinal cavity 122 by its proximal end. This hollow pin 160, for example in titanium, may be a tube adapted for receiving, at a distal end 161, a catheter transporting fluid from/into the chamber 100. In this alternative, the hollow pin 160 is closed, at a proximal end 162. An aperture 163, close to the proximal end 162, opens into the through housing 127, in the area between both blades 111, 112. Thus, the hollow pin 160 is a coupling element that transports fluid from an outside source, via a catheter, towards the inner volume of the chamber or from the inner volume of the chamber towards an outside collector via a catheter. For example, the hollow pin 160 may connect a catheter linked to an external source for bringing fluid inside the chamber or to a pump for sucking the inner of the chamber.

For fluid circulation within the chamber, each intermediate washer 130 comprises a second opening 133. In the embodiments presenting two intermediate washers, the second openings 133 of both intermediate washers are axially lined up the one with the other and with the openings 143 of the membranes 141, 142, and hence with the housing 127. These first openings 143 may have dimensions sensibly equal to the distance between both first openings 131 of the intermediate washers (like represented by the arrow 134 on FIG. 2). Such a line of the openings allows the fluid circulation inside the chamber, fluid coming from the hole 163 in the pin and through the housing 127. In the embodiments of FIGS. 2A-2B, the second openings 133 of the intermediate washers 130 are centrally placed, for example in the middle zone between the first openings 131.

Figure 4:
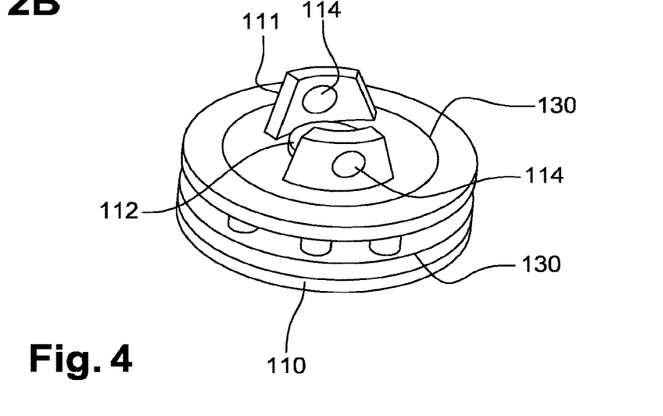
FIG. 4 is a perspective view of a kit connector of the of FIG. 1 without the upper washer, as used in a chamber with semi-permeable membranes.

In addition to the fluid circulation, the hollow pin 160 is primarily used for tightly clipping the upper washer 120 with the bottom washer 110. To this end, each of the blades 111, 112 comprises at least one through-hole 114 located at the free end of said blade, i.e. near the end intended to be inserted in the housings of the upper washer. Examples of blades with through-holes are represented on FIG. 4 wherein the connector 100 is shown without the upper washer 120. These through-holes 114 are arranged to be crossed by the hollow pin 160 in the elevated height 121 of the upper washer. A bottom view of the upper washer 120, on FIG. 5B, represents the hollow pin 160 mounted inside the upper washer and crossing the longitudinal cavity 122. Since the hollow pin 160 crossing also the through-holes 114, the upper washer 120 is tightly clipped with the bottom washer 110. This locking mechanism allows further reducing the ballooning risks. It is to be noted that presence of the elevated height 121 on the upper washer 120 is only needed when the pin 160 also serves to deliver a fluid within the chamber. If the pin serves only to lock the upper 120 and bottom 110 washers together, such elevated height 121 is not compulsory.

In one or more embodiments, and as shown on FIGS. 2A, 2B, 3A, 3B, the connector 100 is sensibly cylindrical, each of the washers 110, 120, 130 being sensibly disk-shaped. The skilled person would understand that other shapes may be considered—e.g. cube shaped—even if the cylindrical shape makes easier the fluid circulation inside the chamber and further reduces the risks of tearing the membranes.

In one or more embodiments, and as represented on FIG. 3A, the connector 100 comprises a sheet 170 provided between the membranes 141, 142, and in particular between both intermediate washers 130. The blades 111 and 112 can serve to maintain the sheet 170 inside the chamber. This sheet 170 creates two half volume spaces S1, S2 within the chamber, and may be made from a biocompatible material or from a not biocompatible material embedded within a silicone layer. It may present protuberances at its surfaces as disclosed above.

While only some selected embodiments have been chosen to illustrate the present invention, it will be apparent to the skilled person from this disclosure that various changes and modifications can be made herein without departing from the scope of the invention as defined in the appended claims. The structures and functions of one embodiment can be adopted in another embodiment. Further, it is not necessary for all advantages to be present in particular embodiments at the same time.

EXAMPLES

Example 1—Improving Tightness of the of the Chamber for Encapsulation by Using New Connectors The tightness of the whole chamber was tested by using three different kinds of connectors, one as disclosed in WO 2012/010767 (previous design) and the two other connectors according to the invention. The main differences of those connectors are given in the table hereinafter.

Material Used for Verification:
1. Connector

TABLE 1 description of the connectors

| Material | Previous design | Invention 1 | Invention 2 |
|---|---|---|---|
| Crossing the whole device | No | Yes | Yes |
| Type of pieces | Molded | Machined | Machined |
| Bump on the intermediate washer (tightness with sealing O-ring) (mm) | None | 0.05 | 0.1 |

NB: Connectors made according to the invention were machined to test the solution prior to manufacture dedicated molds which are more expansive than machine pieces.

A manometer BARFLEX (Baumer; ref. EA4AP3B17R 11012636; 0+2 bars), a syringe pump, a syringe and blue dye are also used.

Protocol:

Two different sizes of devices were manufactured. Each device was assembled with two connectors from the same material and with the same design. Therefore 3 rat size devices and 3 primate size devices were tested.

TABLE 2

Summary of connectors tested on chambers

| Rat size device | Qty | Primate size device | Qty |
|---|---|---|---|
| Previous design | 1 | Previous design | 1 |
| Invention 1 | 1 | Invention 1 | 1 |
| Invention 2 | 1 | Invention 2 | 1 |

One of the two connectors of the assembled devices was plugged to a single lumen 6F catheter to a T-piece.

One of the parts was connected to a syringe placed on a syringe pump. The other part of the T-piece was connected to a manometer.

A single lumen 6F catheter was plugged on the second connector and a subcutaneous port placed at the opposite side of the catheter.

The 20-ml syringe was filled with blue dye to identify easily leakages.

The syringe was then placed to the syringe pump and the type of syringe (20 ml) and the flow rate (50 ml/hr.) were set up with the syringe pump.

A needle was introduced through the silicone septum of the port allowing the filling of the system which means allowing the filling of the catheters and the device until the blue dye drops down from the needle.

Then the syringe pump was stopped and the needle was retrieved from the port.

The syringe pump was restarted and the pressure monitored using the manometer.

When leakages occurred, the maximum pressure was reached and noted. This pressure is then compared with values obtained for the different connectors and sizes of devices tested.

Results Obtained:

The following table compared and summarized the pressures measured during the experiment.

TABLE 3

Pressure measured within the chambers

| Device Size | Connector | Pressure (mbar) |
|---|---|---|
| Rat | Previous design | 20 |
| | Invention 1 | 60 |
| | Invention 2 | 68 |
| Primate | Previous design | 30 |
| | Invention 1 | 47 |
| | Invention 2 | 53 |

CONCLUSION

In every case, the results showed that the connectors according to the invention are more resistant to leakage occurrence therefore are tighter than the connectors of the prior art.

Example 2—Resistance to Ballooning

Chambers with the connectors of the prior art (WO2012/010767) or according to the invention were implanted in pigs and later recovered.

The chambers with the connectors of the prior art show ballooning, while use of the connectors of the invention prevents this phenomenon.

The device was circular with a 64 mm diameter. Two connector systems were placed on a diameter of the device, the center of the connectors being spaced by 25 mm. The diameter of the connectors was 10.4 mm and the height of the connectors was 5.8 mm. Using two (or more) connector systems makes it possible to obtain a "cushion"-like technical effect that effectively limit and prevent ballooning.

The invention claimed is:

1. An implantable chamber (100), having an inner space defined by two semi-permeable membranes sealed together at their periphery,
    for diffusing at least one substance of interest, characterized in that it comprises:
        an upper washer (120) and a bottom washer (110) configured to be oppositely placed on a side and on another side of two semi-permeable membranes (141, 142),
    wherein the two semi-permeable membranes are superposed in between the upper and the bottom washers (120, 110), wherein the upper washer (120) is tightly clipped to the bottom washer (110), wherein the chamber further comprises at least one intermediate washer (130), provided between both membranes, in a plane parallel to the upper and bottom washers' planes and delimiting two superposed half spaces (S1, S2), the upper and bottom washers (120, 110) incorporating the intermediate washer (130) therebetween upon clipping, and wherein:
        the bottom washer (110) comprises at least two blades (111, 112) extending in planes orthogonal to the upper and bottom washers' planes,
        the upper washer (120) comprises housings (126) for receiving free ends of the blades (111, 112) in order to clip the upper washer with the bottom washer, and
        the intermediate washer (130) and the membranes (141, 142) comprise first openings (131, 143) arranged to be crossed by the blades.

2. The implantable chamber according to claim 1, wherein the intermediate washer (130) has at least one side with protrusions (132).

3. The implantable chamber according to claim 1, which further comprises sealing components (150) disposed between the upper washer and one membrane and between the bottom washer and the other membrane.

4. The implantable chamber according to claim 1, wherein the free ends of each of the blades (111, 112) comprises a through-hole (114) adapted to be crossed by a pin (160) in order to tightly clip the upper washer with the bottom washer.

5. The implantable chamber according to claim 4, wherein the pin (160) is a hollow pin extending within the longitudinal cavity (122) and able to transport fluid from an external source into the inner volume of the chamber via the housing (127).

6. The implantable chamber according to claim 5, wherein the intermediate washer (130) comprises at least one second opening (133) allowing diffusion of the fluid within the chamber.

7. The implantable chamber according to claim 6, wherein the second opening (133) is provided in the center of the intermediate washer, the first openings (131) of the intermediate washer (130) being disposed around the second opening.

8. The implantable chamber according to claim 1, wherein the upper washer has an elevated height (121) which defines the housings (126) that cover both blades of the bottom washer.

9. The implantable chamber according to claim 8, wherein the elevated height (121) defines a longitudinal cavity (122) opening between both blades of the bottom washer.

10. The implantable chamber according to claim 1, wherein the upper washer (120), the bottom washer (110) and the intermediate washer (130) are disk-shaped.

11. The implantable chamber according to claim 1, which comprises two intermediate washers (130) provided in parallel planes.

12. A kit connector comprising:
    an upper washer (120) and a bottom washer (110) that can be tightly clipped to each other wherein the bottom washer (110) comprises at least two blades (111, 112) extending in planes orthogonal to the bottom washer (110) plane, wherein the upper washer (120) comprises housings (126) for receiving free ends of the blades (111, 112) and wherein each of the blades (111, 112) comprise, at their free end, a through-hole (114) adapted to be crossed by a pin (160) in order to tightly clip the upper washer (120) with the bottom washer (110), and tight clipping is thus performed by the pin (160) extending across the holes (114) in the free ends of the blades (111, 112), the upper washer (120) and bottom washer (110) being in parallel planes after clipping;

at least one intermediate washer (130), incorporated between the upper and the bottom washers, in a plane parallel to the upper and bottom washers' planes;
optionally sealing components (150) and
a pin (160), that can extend through the through-holes (114) to tightly clip the two washers (110, 120).

13. A method for making the chamber of claim 1, comprising the following steps:
    providing the bottom washer (110) on one side of a first membrane (142), optionally with a sealing means (150) between the bottom washer and the membrane (142);
    crossing the blades (111, 112) of the bottom washer into the first opening (143) of the first membrane;
    providing an intermediate washer (130) above the first membrane (142) with the blades (111, 112) crossing the first openings (131);
    providing a second membrane (141) above the intermediate washer (130), if present, with the blades (111, 112) crossing the first opening (143);
    optionally providing a sealing means (150) above the second membrane (141);
    providing the upper washer (120) upon the second membrane with housings (126) slotted on free ends of the blades; and
    providing a hollow pin (160) crossing the through-hole (114) of each of the blades (111, 112) in order to tightly clip the upper washer (120) with the bottom washer (110).

14. The implantable chamber according to claim 1, wherein the intermediate washer (130) presents protrusions (132) on both sides.

15. The implantable chamber of claim 1, which comprises two intermediate washers (130) provided in parallel planes, each of the intermediate washers comprising protrusions (132) extending on at least one face facing the other intermediate washer.

* * * * *